United States Patent
Lochmann et al.

(10) Patent No.: US 12,258,609 B2
(45) Date of Patent: *Mar. 25, 2025

(54) METHOD FOR PRODUCING GLYCERIDES OF HYDROXYCARBOXYLIC ACIDS

(71) Applicant: KetoLipix Therapeutics GmbH, Hamburg (DE)

(72) Inventors: Dirk Lochmann, Witten (DE); Sebastian Reyer, Witten (DE); Michael Stehr, Witten (DE)

(73) Assignee: KetoLipix Therapeutics GmbH (DE)

( * ) Notice: Subject to any disclaimer, the term of this patent is extended or adjusted under 35 U.S.C. 154(b) by 254 days.

This patent is subject to a terminal disclaimer.

(21) Appl. No.: 17/379,083

(22) PCT Filed: Jan. 23, 2019

(86) PCT No.: PCT/EP2019/051539
§ 371 (c)(1),
(2) Date: Jul. 19, 2021

(87) PCT Pub. No.: WO2020/147978
PCT Pub. Date: Jul. 23, 2020

(65) Prior Publication Data
US 2023/0151395 A1    May 18, 2023

(30) Foreign Application Priority Data

Jan. 17, 2019  (WO) ............... PCT/EP2019/051116

(51) Int. Cl.
| | |
|---|---|
| *C12P 7/625* | (2022.01) |
| *A23L 33/12* | (2016.01) |
| *A61K 31/22* | (2006.01) |
| *A61K 31/225* | (2006.01) |
| *A61P 3/04* | (2006.01) |
| *C07C 67/08* | (2006.01) |
| *C12P 7/62* | (2022.01) |

(52) U.S. Cl.
CPC ............. *C12P 7/625* (2013.01); *A23L 33/12* (2016.08); *A61K 31/22* (2013.01); *A61K 31/225* (2013.01); *A61P 3/04* (2018.01); *C07C 67/08* (2013.01); *C12P 7/62* (2013.01)

(58) Field of Classification Search
CPC .. C12P 7/625; C12P 7/62; A23L 33/12; A61P 3/04; A61K 31/22; A61K 31/225; C07C 67/08

See application file for complete search history.

(56) References Cited

U.S. PATENT DOCUMENTS

| | | | | |
|---|---|---|---|---|
| 5,693,850 A | * | 12/1997 | Birkhahn | A61K 31/22 |
| | | | | 560/189 |
| 2017/0296501 A1 | * | 10/2017 | Lowery | A61P 43/00 |

FOREIGN PATENT DOCUMENTS

| | | |
|---|---|---|
| EP | 0736256 | 10/1996 |
| JP | H0383950 | 4/1991 |
| WO | 9509144 | 4/1995 |
| WO | 0206368 | 1/2002 |
| WO | 2006034361 | 3/2006 |
| WO | 2008005818 | 1/2008 |
| WO | 2013150153 | 10/2013 |
| WO | 2018118369 | 6/2018 |
| WO | 2018132189 | 7/2018 |
| WO | 2018195421 | 10/2018 |
| WO | 2019002828 | 1/2019 |

* cited by examiner

Primary Examiner — Jeffrey S Lundgren
Assistant Examiner — Ibrahim D Bori
(74) Attorney, Agent, or Firm — Edward E. Sowers; Brannon Sowers & Cracraft PC

(57) ABSTRACT

The invention relates to a method for producing glycerides of 3-hydroxybutyric acid as well as the products thus obtained and their use.

16 Claims, No Drawings

METHOD FOR PRODUCING GLYCERIDES OF HYDROXYCARBOXYLIC ACIDS

CROSS-REFERENCES TO RELATED APPLICATIONS

This application is a National Stage filing of International Application PCT/EP 2019/051539 fled Jan. 23, 2019, entitled "METHOD FOR PRODUCING GLYCERIDES OF HYDROXY CARBOXYLIC ACIDS", claiming priority to PCT/EP 2019/051116, filed Jan. 17, 2019. The subject application claims priority to PCT/EP 2019/051539 and PCT/EP 2019/051116, and incorporates all by reference herein, in their entirety.

BACKGROUND OF THE INVENTION

The present invention relates to the field of keto bodies and related metabolism and the therapy of related diseases.

Especially, the present invention relates to a method for producing glycerides of 3-hydroxybutyric acid as well as the reaction products thus obtainable or thus prepared (i.e. glycerides of 3-hydroxybutyric acid) and their use, especially in pharmaceutical compositions, such as drugs or medicaments, or in food and/or food products, as well as their further applications or uses.

Furthermore, the present invention relates to pharmaceutical compositions, especially drugs or medicaments, comprising the reaction products (i.e. glycerides of 3-hydroxybutyric acid) obtainable or produced according to the inventive method, as well as their applications or uses.

Finally, the present invention relates to food and/or food products, especially food supplements, functional foods, novel foods, food additives, food supplements, dietary foods, power snacks, appetite suppressants and strength and/or endurance sports supplements, which comprise the reaction products (i.e. glycerides of 3-hydroxybutyric acid) obtainable or produced according to the inventive method, as well as their applications or uses.

In the human energy metabolism, glucose is the short-term available energy carrier, which is metabolized into energy in the mitochondria by releasing water and carbon dioxide. The glycogen stores of the liver are already emptied during the sleep period during the night. However, especially the human central nervous system (CNS) and the heart require a permanent energy supply.

The physiological alternative to glucose, which is mainly available to the central nervous system, are the so-called keto bodies (synonymously also called ketone bodies).

The term keto body is especially a collective term for three compounds, which are formed mainly in catabolic metabolic states (such as hunger, reduction diets or low-carbohydrate diets) and may lead to ketosis. The term keto bodies includes especially the three compounds acetoacetate (synonymously also referred to as acetacetate) and acetone as well as 3-hydroxybutyric acid (hereinafter also synonymously referred to as beta-hydroxybutyric acid or BHB or 3-BHB) or its salt (i.e. 3-hydroxybutyrate or beta-hydroxybutyrate), the latter being the most important of the three aforementioned compounds. 3-Hydroxybutyric acid or its salt occurs physiologically as the (R)-enantiomer, i.e. as (R)-3-hydroxybutyric acid (synonymously also called (3R)-3-hydroxybutyric acid to emphasize the center of chirality in the 3-position) or its salt.

These keto bodies are also provided physiologically in large amounts from lipids stored in the body by lipolysis during fasting or starvation and replace the energy source glucose almost completely.

The keto bodies are formed in the liver from acetyl coenzyme A (=acetyl-CoA), which originates from beta-oxidation; they represent a transportable form of the acetyl coenzyme A in the human body. However, in order to utilize the keto bodies, the brain and muscles must first adapt by expressing enzymes that are required to convert keto bodies back into acetyl coenzyme A. Especially in times of hunger, the keto bodies contribute a considerable amount to energy production. For example, after some time the brain is able to get by with only a third of the daily amount of glucose.

Physiologically, the keto bodies are synthesized from two molecules of activated acetic acid in the form of acetyl coenzyme A, the normal intermediate product of fatty acid degradation, which is extended using a further acetyl coenzyme A unit and the enzyme HMG-CoA-synthase to the intermediate product 3-hydroxy-3-methyl-glutaryl-CoA (HMG-CoA), wherein finally the HMG-CoA-lyase cleaves off the acetoacetate. These three steps take place exclusively in the mitochondria of the liver (lynen cycle), wherein 3-hydroxybutyrate is finally formed in the cytosol by the D-beta-hydroxybutyrate dehydrogenase. HMG-CoA is also an end product of the degradation of the amino acid leucine, while acetoacetate is formed during the degradation of the amino acids phenylalanine and tyrosine.

Spontaneous decarboxylation turns acetoacetate into acetone; it can occasionally be perceived in the breath of diabetics and dieters. It cannot be further used by the body. However, the proportion of acetone in the keto bodies is small.

Acetoacetate is thus reductively converted into the physiologically relevant form of 3-hydroxybutyric acid or 3-hydroxybutyrate, but can also decompose into the physiologically unusable acetone with the release of carbon dioxide, which is detectable and olfactory perceptible in severe ketosis, a ketoacidosis (e.g. in diabetes mellitus type 1 patients without insulin substitution), in the urine and in the exhaled air.

3-Hydroxybutyric acid is currently used and marketed in the weight training sector as a sodium, magnesium or calcium salt.

However, 3-hydroxybutyric acid is not known or only in very small quantities to humans in evolutionary terms, since plants do not produce 3-hydroxybutyric acid and 3-hydroxybutyric acid in the animal organism only occurs in dead emaciated animals in ketosis, so that 3-hydroxybutyric acid causes nausea when administered orally. 3-Hydroxybutyric acid in the form of free acid and its salts also taste very bitter and can cause severe vomiting and nausea.

Moreover, patients, especially newborns, but also adults cannot permanently tolerate large amounts of salts of 3-hydroxybutyric acid, as these compounds can have a kidney-damaging effect.

In addition, the plasma half-life of 3-hydroxybutyric acid and its salts is so short that even if several grams are taken, the ketosis lasts only for about three to four hours, i.e. patients cannot benefit continuously from a therapy with 3-hydroxybutyric acid or its salts, especially at night. In case of metabolic diseases this can lead to life-threatening situations.

Therefore, in the case of the therapy of such metabolic diseases, so-called medium-chain triglycerides, so-called MCTs, are currently used for ketogenic therapy, i.e. the metabolic conversion of caproic, caprylic and capric acid (i.e. of saturated linear $C_6$-, $C_8$- and $C_{10}$-fatty acids) from the corresponding triglycerides is intended.

Basically, however, from a pharmaceutical and clinical point of view, 3-hydroxybutyric acid is a more effective pharmaceutical-pharmacological target molecule, which, according to the prior art, could in principle be used for the therapy of a large number of diseases, but cannot be used due to its lack of physiological compatibility (e.g. in diseases in connection with a malfunction of the energy metabolism, especially keto-body metabolism, or neurodegenerative diseases such as dementia, Alzheimer's disease, Parkinson's disease, etc., lipometabolic diseases etc.).

The following table illustrates purely exemplary, but by no means limiting, potential therapy options or possible indications for the active ingredient 3-hydroxybutyric acid.

| Indication | Therapeutic effect |
| --- | --- |
| Traumatic brain injury | Under BHB the apoptosis and necrosis rate of nerve cells decreases. |
| Stroke | Under BHB the apoptosis and necrosis rate of nerve cells decreases. |
| Refeeding syndrome | In case of anorexia, discontinuation of enteral or parenteral nutrition and after long periods of hunger, the consumption of starch or glucose can lead to death (see also WHO scheme peanut paste). BHB can be used here as a therapeutic agent to achieve normal food intake more quickly. |
| Appetite suppressant | BHB suppresses the feeling of hunger in the central nervous system (CNS). |
| Epilepsy | Conventional ketogenic diet to significantly reduce the frequency of seizures has extremely poor patient tolerance. BHB offers an immediately effective alternative here. |
| Alzheimer's disease, dementia | Under BHB patients show better cognitive performance. BHB is also effective in the prevention of neurodegenerative diseases. |
| Disorders of fatty acid oxidation (e.g. electron transfer protein defect) | Compensation of a nutrient deficiency in case of defect in energy metabolism. |

Therefore, it is desirable from a pharmaceutical and clinical point of view to be able to find effective precursors or metabolites which physiologically allow direct or indirect access to 3-hydroxybutyric acid or its salts, especially in the physiological metabolism of the human or animal body.

Consequently, the prior art has not lacked attempts to find physiologically suitable precursors or metabolites for 3-hydroxybutyric acid or its salts. So far, however, no efficient compounds have been found in the prior art. Also, access to such compounds is not or not readily possible according to the prior art.

BRIEF SUMMARY OF THE INVENTION

The problem underlying the present invention is thus the provision of an efficient method for producing physiologically suitable or physiologically compatible precursors and/or metabolites of 3-hydroxybutyric acid (i.e. beta-hydroxybutyric acid or BHB or 3-BHB) or their salts.

Such method should especially make the respective BHB precursors and/or BHB metabolites accessible in an efficient way, especially in larger quantities and without significant amounts of toxic by-products.

In a completely surprising way, the applicant has now discovered that glycerides of 3-hydroxybutyric acid (beta-hydroxybutyric acid or BHB or 3-BHB) represent an efficient and physiologically effective or physiologically compatible precursor and/or metabolite for the keto body 3-hydroxybutyric acid or its salts and has in this context been able to find or develop an efficient method for producing these compounds, which allows direct and effective, especially economic as well as industrially feasible access to these compounds.

To solve the problem described above, the present invention therefore proposes—according to a first aspect of the present invention—a method for producing of glycerides of 3-hydroxybutyric acid (beta-hydroxybutyric acid or BHB or 3-BHB); further, especially special and/or advantageous embodiments of the inventive method are provided.

Furthermore, the present invention relates—according to a second aspect of the present invention—to a reaction product obtainable according to the inventive method or a mixture of at least two glycerides of 3-hydroxybutyric acid; further, especially special and/or advantageous embodiments of this aspect of the invention are provided.

Likewise, the present invention—according to a third aspect of the present invention—relates to a pharmaceutical composition, especially a drug or medicament; further, especially special and/or advantageous embodiments of this aspect of the invention are provided.

Furthermore, the present invention—according to a fourth aspect of the present invention—relates to a reaction product or mixture according to the invention for the prophylactic and/or therapeutic treatment or for use in the prophylactic and/or therapeutic treatment of diseases of the human or animal body.

Furthermore, the present invention—according to a fifth aspect of the present invention—relates to the use of a reaction product or a mixture according to the invention for the prophylactic and/or therapeutic treatment or for producing a medicament for the prophylactic and/or therapeutic treatment of diseases of the human or animal body.

Furthermore, the present invention—according to a sixth aspect of the present invention—relates to the use of a reaction product or mixture.

Furthermore, the present invention—according to a seventh aspect of the present invention—relates to a food and/or food product; further, especially special and/or advantageous embodiments of the food and/or food product according to the invention are provided.

Finally, the present invention—according to an eighth aspect of the present invention—relates to the use of a reaction product or mixture according to the invention in a food and/or a food product; further, especially special and/or advantageous embodiments of the use according to the invention are provided.

It goes without saying that following features, embodiments, advantages and the like, which are subsequently listed below only with regard to one aspect of the invention for the purpose of avoiding repetition, naturally also apply accordingly to the other aspects of the invention, without this requiring a separate mention.

Furthermore, it goes without saying that individual aspects and embodiments of the present invention are also considered disclosed in any combination with other aspects and embodiments of the present invention and, especially, any combination of features and embodiments, as it results from back references of all patent claims, is also considered extensively disclosed with regard to all resulting combination possibilities.

With respect to all relative or percentage weight-based data provided below, especially relative quantity or weight data, it should further be noted that within the scope of the present invention these are to be selected by the person skilled in the art such that they always add up to 100% or 100% by weight, respectively, including all components or ingredients, especially as defined below; however, this is self-evident for the person skilled in the art.

In addition, the skilled person may, if necessary, deviate from the following range specifications without leaving the scope of the present invention.

In addition, it applies that all values or parameters or the like specified in the following can be determined or identified in principle with standardized or explicitly specified determination methods or otherwise with the determination or measurement methods that are otherwise familiar to a person skilled in the art.

Having stated this, the present invention will be described in more detail hereinafter:

DETAILED DESCRIPTION OF THE INVENTION

The subject of the present invention—according to a first aspect of the present invention—is thus a method for producing glycerides of 3-hydroxybutyric acid (beta-hydroxybutyric acid, BHB or 3-BHB),
wherein at least one compound of the general formula (I)

$$CH_3-CH(OH)-CH_2-C(O)OR^1 \qquad (1)$$

wherein in the general formula (I) the radical $R^1$ represents hydrogen or $C_1$-$C_4$ alkyl, especially $C_1$-$C_4$ alkyl, preferably methyl or ethyl, more preferably ethyl,
is reacted with glycerol (1,2,3-propanetriol) of formula (II)

$$CH_2(OH)-CH(OH)-CH_2(OH) \qquad (II)$$

so that, as a reaction product, one or more glycerides of 3-hydroxybutyric acid of the general formula (III)

$$CH_2(OR^2)-CH(OR^3)-CH_2(OR^4) \qquad (III)$$

are obtained, wherein in the general formula (III) the radicals $R^2$, $R^3$ and $R^4$, each independently of one another, represent hydrogen or a radical of formula $CH_3-CH(OH)-CH_2-C(O)-$, however, with the proviso that at least one of the radicals $R^2$, $R^3$ and $R^4$ does not represent hydrogen.

As stated above, the applicant has, quite surprisingly, discovered that the glycerides of 3-hydroxybutyric acid (hereinafter briefly referred to as "BHB glycerides"/"3-BHB glycerides" or "BHB esters"/"3-BHB esters" for short) thus produced are efficient, since physiologically compatible precursors and/or metabolites of 3-hydroxybutyric acid or their salts, which can also be used in larger quantities in pharmaceutical or clinical applications because they are physiologically compatible.

The above-mentioned glycerides of 3-hydroxybutyric acid, which are accessible for the first time in an efficient manner through the production method according to the invention, represent a physiologically and pharmacologically relevant alternative to free 3-hydroxybutyric acid or its salts.

The production of glycerides of 3-hydroxybutyric acid by means of conventional organic synthesis is complex and costly, since 3-hydroxybutyric acid has an increased tendency to polymerize and to undergo other undesirable side reactions (e.g. dehydration, decomposition, etc.). Within the scope of the present invention, it was possible for the first time to provide an efficiently working production method with which glycerides of 3-hydroxybutyric acid can be produced without undesired side reactions, especially in a single step.

The inventive method thus makes it possible for the first time to provide non-toxic esters of 3-hydroxybutyric acid from known, commercially available and above all physiologically harmless components or educts (starting compounds). The resulting glycerides can be broken down physiologically, especially in the stomach and/or bowl, and release or generate the target molecule "3-hydroxybutyric acid" or its salts as active ingredient or active component.

In addition, the aforementioned glycerides of 3-hydroxybutyric acid also comprise an acceptable taste to ensure compatibility even when administered orally in larger quantities over a longer period of time (e.g. administration of 50 g daily dose or more).

Similarly, the production method according to the invention makes it possible to provide the glycerides of 3-hydroxybutyric acid free from toxic impurities.

In addition, with appropriate starting materials, the method can also be carried out enantioselectively. For example, according to the invention, the production method allows the biologically relevant form, i.e. the (R)-enantiomer, to be enriched, especially by enzyme catalysis, as not to burden the renal system of patients when administered orally (i.e. elimination via the kidneys). In principle, however, it is also possible, and under certain conditions may be useful, to enrich the (S)-enantiomer.

In addition, the production method according to the invention, including optional further processing or purification steps, can be operated economically and can also be implemented on a large scale.

Especially, the inventive production method uses commercially available starting compounds and furthermore allows a relatively simple process management even in case of large-scale implementation.

In contrast to conventional prior art production methods, which use complex starting compounds and corresponding protective group chemistry, e.g. diketenes (e.g. WO 95/09144 A1 or WO 90/02549 A1), or complex multi-stage syntheses (e.g. U.S. Pat. No. 6,306,828 B1), the production method according to the invention does not use such complex starting materials and uses only a single step. Nevertheless, excellent yields are achieved in accordance with the invention, wherein the formation of by-products is minimized or avoided.

In addition, the inventive method is simple and economical. Especially, the method according to the invention is usually carried out in the absence of solvents and/or without any solvent (i.e. as a reaction in mass or as a reaction in substance or as a so-called bulk reaction); consequently, the reaction products obtained are not contaminated with solvent and no solvent has to be removed and disposed of or recycled in a costly and energy-intensive manner after the method or reaction has been carried out. Furthermore, no toxic by-products are formed.

The production method according to the invention usually results in a mixture of different glycerides of 3-hydroxybutyric acid, i.e. of at least two of mono-, di- and/or triglycerides of 3-hydroxybutyric acid. The resulting raw reaction product or raw glyceride mixture can be purified by known methods, especially by removing any remaining starting compounds and/or any by-products present, and—if desired—can be separated by known methods, especially by distillation and/or chromatography (e.g. fractionation into the individual glycerides, i.e. mono-, di- and triglycerides of 3-hydroxybutyric acid, or else fractionation into fractions with enriched and depleted portions of individual glycerides, or else fractionation into a mixture of mono- and diglycerides on the one hand and the triglyceride on the other hand, or else fractionation into the monoglyceride on the one hand and a mixture of di- and triglycerides on the other hand, etc.).

According to a particular embodiment of the present invention, the compound of the general formula (I) can be used either in racemic form or in the form of the (R)-enantiomer.

The (R)-configuration refers to the chiral carbon atom in the 3-position of the compound of the general formula (I).

According to the invention, it is preferred when, in the general formula (I), the radical $R^1$ represents ethyl.

In other words, according to the invention, it is preferred that, as a compound of the general formula (I), 3-hydroxybutyric acid ethyl ester (ethyl 3-hydroxybutyrate) of the formula $CH_3-CH(OH)-CH_2-C(O)OC_2H_5$ is used.

This enables particularly efficient process control and high yields with minimized or suppressed by-product formation. In addition, the 3-hydroxybutyric acid ethyl ester is also commercially available in large quantities and can also be converted more efficiently than the free acid (i.e. 3-hydroxybutyric acid). Especially, the 3-hydroxybutyric acid ethyl ester can be obtained on a large scale as a starting compound, e.g. by Claisen condensation of ethyl acetate.

Especially, in the inventive method, the reaction is carried out in the absence of solvents and/or without any solvent. This means that the reaction is carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

According to a particular embodiment of the present invention, the reaction can be carried out in the presence of a catalyst, especially an enzyme and/or a metal-containing and/or metal-based, acidic or basic catalyst, preferentially in the presence of an enzyme. In this particular embodiment, it is preferred that the catalyst is recycled after the reaction However, as an alternative to this particular embodiment, it is also possible to carry out the reaction autocatalytically or in the absence of a catalyst. However, the use of a catalyst is preferred.

As mentioned above, according to the invention, the reaction can be carried out in the presence of an enzyme as catalyst.

In this context, the enzyme can especially be selected from synthetases (ligases), catalases, esterases, lipases and combinations thereof. According to the invention, synthetases (synonymously ligases) are especially enzymes from the class of ligases; ligases are enzymes which catalyze the linking of two or more molecules by a covalent bond. Catalases in the sense of the present invention are especially enzymes which are capable of converting hydrogen peroxide to oxygen and water. The term esterases refers in particular to enzymes which are capable of hydrolytically splitting esters into alcohol and acid (saponification); these are thus especially hydrolases, wherein fat splitting esterases are also called lipases. Lipases in the sense of the present invention are especially enzymes which are capable of splitting free fatty acids from lipids such as glycerides (lipolysis).

Within the scope of the present invention, the enzyme used as catalyst can especially be derived from *Candida antarctica, Mucor miehei (Rhizomucor miehei), Thermomyces lanuginosus, Candida rugosa, Aspergillus oryzae, Pseudomonas cepacia, Pseudomonas fluorescens, Rhizopus delemar* and *Pseudomonas* sp. and combinations thereof, preferentially from *Candida antarctica, Mucor miehei (Rhizomucor miehei)* and *Thermomyces lanuginosus*.

According to a specific embodiment, the enzyme can be used in immobilized form, immobilized on a carrier, preferentially on a polymeric carrier, preferably on a polymeric organic carrier, more preferably with hydrophobic properties, even more preferably on a poly(meth)acrylic resin-based carrier.

As explained hereinabove with respect to the use of a catalyst in general, when an enzyme is used as a catalyst, it is preferred to recycle the enzyme after the reaction.

If the reaction is carried out in the presence of an enzyme as a catalyst within the framework of the inventive production method, it is preferred if the reaction is carried out at temperatures in the range of from 10° C. to 80° C., especially in the range of from 20° C. to 80° C., preferentially in the range of from 25° C. to 75° C., more preferably in the range of from 45° C. to 75° C., even more preferably in the range of from 50° C. to 70° C.

In case of using an enzyme as a catalyst, the amount of the enzyme used can vary within wide range. Especially, the enzyme can be used in amounts, based on the total amount of the starting compounds of formulae (I) and (II), in the range of from 0.001 to 20% by weight, especially in the range of from 0.01 to 15% by weight, preferentially in the range of from 0.1 to 15% by weight, preferably in the range of from 0.5 to 10% by weight.

Nevertheless, it may be necessary to deviate from the above-mentioned amounts in individual cases or for specific applications without leaving the scope of the present invention.

If, according to a particular embodiment of the present invention, the reaction is carried out in the presence of an enzyme as a catalyst, the applied pressure range may also vary within a wide range. Especially, if the reaction is carried out in the presence of an enzyme as a catalyst, the reaction can be carried out in the presence of an enzyme as a catalyst at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

According to an alternative embodiment of the present invention, the reaction can be carried out in the presence of a metal-containing and/or metal-based, acidic or basic catalyst.

According to this alternative embodiment of the present invention, according to which the reaction is carried out in the presence of a metal-containing and/or metal-based, acidic or basic catalyst, the catalyst can especially be selected from (i) basic catalysts, especially alkali or alkaline earth hydroxides and alkali or alkaline earth alcoholates, such as NaOH, KOH, LiOH, $Ca(OH)_2$, NaOMe, KOMe and Na(OBu-tert.), (ii) acidic catalysts, especially mineral acids, and organic acids, such as sulfuric acid, hydrochloric acid, phosphoric acid, nitric acid, sulfonic acids, methanesulfonic acid, para-toluenesulfonic acid and carboxylic acids, (iii) Lewis acids, especially Lewis acids based on titanium, tin, zinc and aluminum compounds, such as titanium tetrabutylate, tin acids, zinc acetate, aluminum trichloride and aluminum tri-isopropyl, and (iv) heterogeneous catalysts, especially based on mineral silicates, germanates, carbonates and aluminum oxides, such as zeolites, montmorillonites, mordenites, hydrotalcites and aluminas, and combinations thereof.

According to this embodiment, especially an alkali or alkaline earth alcoholate can be used as a catalyst.

Especially, also according to this embodiment it is preferred if the catalyst based on the metal-containing and/or metal-based, acidic or basic catalyst is recycled after the reaction.

If, according to the particular embodiment of the present invention, the reaction is carried out in the presence of a metal-containing and/or metal-based, acidic or basic catalyst, the temperatures can be varied within a wide range. Especially, the reaction can be carried out in the presence of a metal-containing and/or metal-based, acidic or basic catalyst at temperatures in the range of from 20° C. to 150° C., especially in the range of from 50° C. to 140° C., preferentially in the range of from 70° C. to 130° C., more preferably in the range of from 80° C. to 125° C., even more preferably in the range of from 100° C. to 120° C.

Furthermore, also according to this embodiment, the catalyst (i.e. the metal-containing and/or metal-based, acidic or basic catalyst) can also be varied within wide quantity ranges: For example, the catalyst based on a metal-containing and/or metal-based, acidic or basic catalyst can be used in amounts, based on the total amount of the starting compounds of formulae (I) and (II), in the range of from 0.01 to 30% by weight, especially in the range of from 0.05 to 15% by weight, preferentially in the range of from 0.1 to 15% by weight, preferably in the range of from 0.2 to 10% by weight. Nevertheless, it is possible to deviate from the above-mentioned amounts for specific applications or individual cases without leaving the scope of the present invention.

If, according to this particular embodiment of the present invention, the reaction is carried out in the presence of a metal-containing and/or metal-based, acidic or basic catalyst, the pressure range can equally vary within a wide range: Especially, the reaction can be carried out in the presence of a metal-containing and/or metal-based, acidic or basic catalyst at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

As far as the quantity of starting materials or starting compounds is concerned, this can also be varied within a wide range.

Taking into account process economy and optimization of the course of the method, especially with regard to the minimization of by-products, it is advantageous if the compound of the general formula (I), based on the hydroxyl groups of the glycerol of formula (II), is used in molar amounts in a range of from equimolar amount up to a molar excess of 200 mol-%, especially in a range of from equimolar amount up to a molar excess of 150 mol-%, preferentially in a range of from equimolar amount up to a molar excess of 100 mol-%.

Similarly, taking into account process economy and optimization of the course of the method, especially with regard to minimizing by-products, it is advantageous if the compound of the general formula (I) and the glycerol of the formula (II) are used in a molar ratio of compound of the general formula (I)/glycerol of the formula (II) in a range of from 1:1 to 10:1, especially in a range of from 2:1 to 8:1, preferably in a range of from 3:1 to 6:1.

According to a more preferred embodiment of the present invention, the present invention relates to a method for producing glycerides of 3-hydroxybutyric acid (beta-hydroxybutyric acid, BHB or 3-BHB), especially a method as defined hereinabove,
wherein at least one compound of formula (Ia)

$$CH_3-CH(OH)-CH_2-C(O)OC_2H_5 \qquad (Ia)$$

is reacted with glycerol (1,2,3-propanetriol) of formula (II)

$$CH_2(OH)-CH(OH)-CH_2(OH) \qquad (II)$$

so that as a reaction product one or more glycerides of 3-hydroxybutyric acid of the general formula (III)

$$CH_2(OR^2)-CH(OR^3)-CH_2(OR^4) \qquad (III)$$

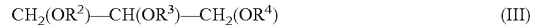

are obtained, wherein in the general formula (III) the radicals $R^2$, $R^3$ and $R^4$, each independently of one another, represent hydrogen or a radical of formula $CH_3-CH(OH)-CH_2-C(O)-$, however, with the proviso that at least one of the radicals $R^2$, $R^3$ and $R^4$ does not represent hydrogen.

In this context, the reaction can be carried out especially in the presence of a catalyst, especially an enzyme, especially as defined above, especially as described above and/or especially under the conditions described above.

This procedure leads to a particularly good process efficiency and process economy, especially connected with high yields and a minimization of by-product formation.

The method which is particularly preferred according to the invention is illustrated by the following reaction or synthesis scheme (wherein in this reaction or synthesis scheme the radicals $R^2$, $R^3$ and $R^4$, each independently of the others, represent hydrogen or a radical of the formula $CH_3-CH(OH)-CH_2-C(O)-$, however, with the proviso that at least one of the radicals $R^2$, $R^3$ and $R^4$ does not represent hydrogen):

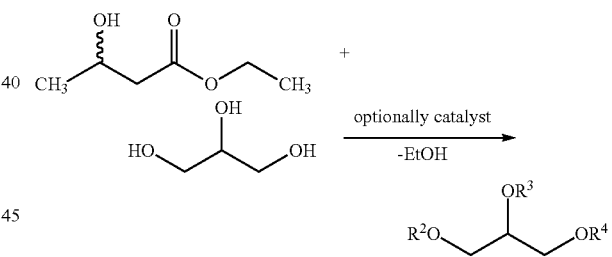

In the context of the inventive production method, during the reaction the compound according to the general formula (IV)

$$R^1-OH \qquad (IV)$$

is formed, wherein in the general formula (IV) the radical $R^1$ represents hydrogen or $C_1$-$C_4$ alkyl, especially $C_1$-$C_4$ alkyl, preferably methyl or ethyl, more preferably ethyl. In other words, water or $C_1$-$C_4$ alcohols are formed in the course of the reaction, depending on the starting compound of the general formula (I).

In this context, it is preferred or advantageous if the compound according to the general formula (IV) (i.e. in particular water or $C_1$-$C_4$ alcohols) is withdrawn from the reaction, especially continuously withdrawn, especially by means of preferentially continuous removal by distillation. In this way, the reaction equilibrium is efficiently shifted to the reaction product side. It also comprises the minimization or prevention of by-product formation.

According to the invention, as a reaction product, one or more glycerides of 3-hydroxybutyric acid of the general formula (III)

$$CH_2(OR^2)—CH(OR^3)—CH_2(OR^4) \quad (III)$$

are obtained, wherein in the general formula (III) the radicals $R^2$, $R^3$ and $R^4$, each independently of one another, represent hydrogen or a radical of formula $CH_3$—CH(OH)—$CH_2$—C(O)—, however, with the proviso that at least one of the radicals $R^2$, $R^3$ and $R^4$ does not represent hydrogen Especially, in the production method according to the invention, two or three different glycerides of 3-hydroxybutyric acid of general formula (III), as defined above, are obtained.

Especially, within the framework of the present invention, a mixture of at least two different glycerides of 3-hydroxybutyric acid of general formula (III), as defined above, is obtained.

In accordance with a particular embodiment of the present invention, a mixture of mono-, di- and/or triglycerides of 3-hydroxybutyric acid is obtained within the scope of the production method according to the invention.

In accordance with the invention, as a reaction product, a mixture of mono-, di- and/or triglycerides of 3-hydroxybutyric acid is obtained within the scope of the inventive production method. Especially, the mixture may comprise monoglycerides of 3-hydroxybutyric acid (3-BHB-MG), diglycerides of 3-hydroxybutyric acid (3-BHB-DG) and triglycerides of 3-hydroxybutyric acid (3-BHB-TG) in a weight ratio of 3-BHB-MG/3-BHB-DG/3-BHB-TG in the range of 10-80/10-70/0.1-20, especially in the range of 20-70/20-60/0.5-15.

In addition, any desired mixture can be prepared or the respective pure glycerides (i.e. pure monoglyceride of 3-hydroxybutyric acid or pure diglyceride of 3-hydroxybutyric acid or pure triglyceride of 3-hydroxybutyric acid) can be obtained by means of common workup and/or separation methods (e.g. chromatography, distillation, etc.). Also pure mixtures of monoglyceride(s) of 3-hydroxybutyric acid and diglyceride(s) of 3-hydroxybutyric acid can be obtained in this way.

Within the scope of the inventive production method, the composition of the reaction product, especially the presence of the various glycerides of 3-hydroxybutyric acid of the general formula (III) and the proportion thereof, may be controlled and/or regulated by means of the reaction conditions. Especially, this can be accomplished by selecting the reaction temperature (conversion temperature) and/or by selecting the reaction pressure (conversion pressure) and/or by providing a catalyst and selecting such catalyst with respect to the type and/or amount and/or by selecting the amounts of the starting compounds (educts) and/or by providing the removal of the compound according to the general formula (IV) as defined above.

After the reaction, the reaction product obtained can be subjected to further purification or work-up steps.

In this context, the reaction product obtained can be fractionated after the reaction has been performed, especially fractionated by distillation. Especially, in this embodiment, the reaction product can be at least separated into a first, especially low-boiling fraction, which comprises a high proportion of mono- and diglycerides of 3-hydroxybutyric acid and a low proportion of triglycerides of 3-hydroxybutyric acid, and a second, especially high-boiling fraction, which comprises a low proportion of monoglycerides of 3-hydroxybutyric acid and a high proportion of di- and triglycerides of 3-hydroxybutyric acid In this respect, the first, especially low-boiling fraction may especially have a weight ratio of 3-BHB-MG/3-BHB-DG/3-BHB-TG in the range of 70-95/5-30/0.01-2, especially in the range of 75-85/10-25/0-1; especially, the second, especially high-boiling fraction may have a weight-related ratio of 3-BHB-MG/3-BHB-DG/3-BHB-TG in the range of 5-30/20-80/5-40, especially in the range of 5-20/40-75/10-30.

According to a particular embodiment of the present invention, unreacted starting compounds of formulae (I) and/or (II) can be separated from the reaction product and are subsequently recycled.

As mentioned hereinbefore, the method according to the invention is usually carried out in the absence of solvents and/or without any solvent (i.e. as a reaction in mass or as a reaction in substance or as a so-called bulk reaction). This has the advantage that the reaction products obtained are not contaminated with solvent and no solvent has to be removed and disposed of or recycled in a costly and energy-intensive manner after the method or reaction has been carried out. Surprisingly, the method or reaction nevertheless proceeds with high conversions and yields and at least essentially without significant by-product formation.

A further subject-matter—according to a second aspect of the present invention—is the reaction product obtainable by the method according to the invention.

Especially, an subject-matter of the present invention is a reaction product (i.e. a (chemical) product or product mixture) which contains one or more glycerides of 3-hydroxybutyric acid of the general formula (III)

$$CH_2(OR^2)—CH(OR^3)—CH_2(OR^4) \quad (III)$$

wherein in the general formula (III) the radicals $R^2$, $R^3$ and $R^4$, each independently of one another, represent hydrogen or a radical of formula $CH_3$—CH(OH)—$CH_2$—C(O)—, however, with the proviso that at least one of the radicals $R^2$, $R^3$ and $R^4$ does not represent hydrogen.

The subject-matter of the present invention is especially a mixture of at least two glycerides of 3-hydroxybutyric acid of the general formula (III) obtainable by the inventive method $$CH_2(OR^2)—CH(OR^3)—CH_2(OR^4) \quad (III)$$

wherein in the general formula (III) the radicals $R^2$, $R^3$ and $R^4$, each independently of one another, represent hydrogen or a radical of formula $CH_3$—CH(OH)—$CH_2$—C(O)—, however, with the proviso that at least one of $R^2$, $R^3$ and $R^4$ does not represent hydrogen.

According to a particular embodiment of the present invention, the subject-matter of the present invention is a mixture comprising two or three different glycerides of 3-hydroxybutyric acid of general formula (III) as defined above, obtainable by the inventive method.

According to another particular embodiment of the present invention, the subject-matter of the present invention is a mixture comprising at least two different glycerides of 3-hydroxybutyric acid of general formula (III) as defined above, obtainable by the inventive method.

According to another particular embodiment of the present invention, the subject-matter of the present invention is a mixture comprising a mixture of mono-, di- and/or triglycerides of 3-hydroxybutyric acid, obtainable by the inventive method.

According to another particular embodiment of the present invention, the subject-matter of the present invention is a mixture of mono-, di- and/or triglycerides of 3-hydroxybutyric acid obtainable by the method according to the invention. Especially, the mixture may comprise monoglycerides of 3-hydroxybutyric acid (3-BHB-MG), diglycerides of 3-hydroxybutyric acid (3-BHB-DG) and triglycerides of 3-hydroxybutyric acid (3-BHB-TG) in a weight ratio of 3-BHB-MG/3-BHB-DG/3-BHB-TG in the range of 10-80/10-70/0.1-20, especially in the range of 20-70/20-60/0.5-15.

According to another particular embodiment of the present invention, the subject-matter of the present invention is a mixture of mono-, di- and/or triglycerides of 3-hydroxybutyric acid obtainable according to the inventive method, wherein the mixture of mono-, di- and/or triglycerides of 3-hydroxybutyric acid comprises the mono-, di- and/or triglycerides of 3-hydroxybutyric acid in a weight ratio of 3-BHB-MG/3-BHB-DG/3-BHB-TG in the range of 70-95/5-30/0.01-2, especially in the range of 75-85/10-25/0-1. This special mixture can be obtained especially by fractional distillation as a low-boiling fraction from the reaction product mixture.

Furthermore, according to another special embodiment of the present invention, the subject-matter of the present invention is a mixture obtainable according to the inventive method, wherein the mixture comprises a mixture of mono-, di- and/or triglycerides of 3-hydroxybutyric acid, wherein the mixture of mono-, di- and/or triglycerides of 3-hydroxybutyric acid comprises the mono-, di- and/or triglycerides of 3-hydroxybutyric acid in a weight ratio of 3-BHB-MG/3-BHB-DG/3-BHB-TG in the range of 5-30/20-80/5-40, especially in the range of 5-20/40-75/10-30. This special mixture can be obtained especially by fractional distillation as a heavy boiling fraction from the reaction product mixture.

As mentioned above, any mixture can be prepared by the usual workup and/or separation methods (e.g. chromatography, distillation, etc.) or the respective pure glycerides (i.e. pure monoglyceride of 3-hydroxybutyric acid or pure diglyceride of 3-hydroxybutyric acid or pure triglyceride of 3-hydroxybutyric acid) can be obtained. Also pure mixtures of monoglycerides of 3-hydroxybutyric acid and diglycerides of 3-hydroxybutyric acid can be obtained in this way.

The subject-matter of the present invention according to a further special embodiment of the present invention is therefore also a mixture of monoglyceride(s) of 3 hydroxybutyric acid and diglyceride(s) of 3-hydroxybutyric acid.

According to another special embodiment, the triglyceride of 3-hydroxybutyric acid is also a subject-matter of the present invention.

The reaction product or mixture of glycerides obtained according to the invention comprises a number of advantages and special features compared to the prior art:

As the applicant has surprisingly found out, the reaction product or glyceride mixture obtainable according to the invention is suitable as a precursor or metabolite of 3-hydroxybutyric acid or its salts, since on the one hand it is converted physiologically, especially in the gastrointestinal tract, to 3-hydroxybutyric acid or its salts and on the other hand it simultaneously comprises a good physiological compatibility or tolerability, especially with regard to non-toxicity and acceptable organoleptic properties.

In addition, the reaction product or glyceride mixture according to the invention is easily accessible or available on a large scale on a synthetic basis, even on a commercial scale, and with the required pharmaceutical or pharmacological quality.

Additionally, the reaction product or glyceride mixture according to the invention can, if necessary, be provided in enantiomerically pure or enantiomerically enriched form.

The reaction product or glyceride mixture according to the invention thus represents an efficient pharmacological drug target in the context of keto-body therapy of the human or animal body.

A further subject-matter of the present invention—according to a third aspect of the present invention—is a pharmaceutical composition, especially a drug or medicament, which comprises a reaction product, as defined hereinabove, obtainable according to the inventive production method and/or a mixture, as defined hereinabove, obtainable according to the inventive production method.

Especially, according to this aspect of the invention, the present invention relates to a pharmaceutical composition for the prophylactic and/or therapeutic treatment or for use in the prophylactic and/or therapeutic treatment of diseases of the human or animal body. This may especially concern diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Again, a further subject-matter of the present invention—according to a fourth aspect of the present invention—is a reaction product, as defined hereinabove, obtainable according to the inventive production method and/or a mixture, as defined hereinabove, obtainable according to the inventive production method for the prophylactic and/or therapeutic treatment or for use in the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to a fifth aspect of the present invention—is the use of a reaction product, as defined hereinabove, obtainable according to the inventive production method and/or a mixture, as defined hereinabove, obtainable according to the inventive production method for the prophylactic and/or therapeutic treatment or for producing a pharmaceutical for the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VLFAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to a sixth aspect of the present invention—is the use of a reaction product, as defined hereinabove, obtainable according to the inventive production method and/or of a mixture, as defined hereinabove, obtainable according to the inventive production method for the prophylactic and/or therapeutic treatment or for producing a medicament for the prophylactic and/or therapeutic treatment of or for the application for catabolic metabolic states, such as hunger, diets or low-carbohydrate nutrition.

Likewise, a further subject-matter of the present invention—according to a seventh aspect of the present invention—is a food and/or a food product, which comprises a reaction product, as defined hereinabove, obtainable according to the inventive production method and/or a mixture, as defined hereinabove, obtainable according to the inventive production method.

According to a particular embodiment, the food and/or the food product may essentially be a dietary supplement, a functional food, a novel food, a food additive, a food supplement, a dietary food, a power snack, an appetite suppressant or a strength and/or endurance sport supplement.

Finally, yet another subject-matter of the present invention—according to an eighth aspect of the present invention—is the use of a reaction product, as defined hereinabove, obtainable according to the inventive production method and/or a mixture, as defined hereinabove, obtainable according to the inventive production method in a food and/or a food product.

According to this aspect of the invention, the food and/or the food product may especially be a dietary supplement, a functional food, a novel food, a food additive, a food supplement, a dietary food, a power snack, an appetite suppressant or a strength and/or endurance sports supplement.

Further embodiments, modifications and variations of the present invention are readily recognizable or realizable by a person skilled in the art when reading the description, without leaving the scope of the present invention.

The present invention is illustrated by the following examples, which are not intended to limit the present invention in any way, but only to explain the exemplary and non-limiting implementation and configuration of the present invention.

EXAMPLES

Abbreviations Used

3-BHB-ethyl=3-hydroxybutyric acid ethyl ester (starting compound)
Glyc.=glycerol (starting compound)
3-BHB-MG=monoglyceride of 3-hydroxybutyric acid (reaction product according to the invention)
3-BHB-DG=diglyceride of 3-hydroxybutyric acid (reaction product according to the invention)
3-BHB-TG=triglyceride of 3-hydroxybutyric acid (reaction product according to the invention)
3-BHB-dimer-MG=monoglyceride of the dimer of 3-hydroxybutyric acid (reaction by-product)
3-BHB-dimer-DG=diglyceride of the dimer of 3-hydroxybutyric acid (reaction by-product)
3-BHB-FS=3-hydroxybutyric acid (reaction by-product)
3-BHB-dimer-FS=dimer of 3-hydroxybutyric acid (reaction by-product)
3-BHB dimer=dimer of 3-hydroxybutyrate (reaction by-product)
n.d.=not determined Examples of Production The production method in accordance with the invention is illustrated by the following examples.
Production of 3-BHB Mono-, Di- and Triglyceride Mixtures In a 500-ml-multi-neck flask with dephlegmator (partial condenser) and distillation bridge, 300 g (R)/(S)-3-hydroxybutyric acid ethyl ester (i.e. racemic ester), 50 g glycerol and 3.3 g immobilized enzyme (CALB lipase on polymer support, derived from *Candida antarctica*, e.g. Novozym® 435 from Sigma-Aldrich or Merck or Lipozym® 435 from Strem Chemicals, Inc.) are provided. The reaction mixture is stirred at 70° C. and under vacuum (<500 mbar) for 36 h. The enzyme is then filtered out and recycled and the excess ethyl 3-hydroxybutyrate is distilled off under vacuum. If necessary, the residue obtained is steam-treated in a high vacuum for 2 to 4 h (steam temperature: 160° C.).

A reaction product based on a mixture of mono-, di- and triglycerides of 3-hydroxybutyric acid with the following composition is obtained: 16% 3-BHB monoglyceride, 58.5% 3-BHB diglyceride and 25% 3-BHB triglyceride, which still contains 0.5% 3-hydroxybutyric acid as a reaction by-product. The characterization is performed by means of GC, GC-MS and NMR.

During the purification process, the 3-hydroxybutyric acid is removed, so that the pure mixture is obtained. Part of the mixture is separated by chromatography so that the various glycerides are obtained as pure substances (i.e. pure 3-BHB-monoglyceride, pure 3-BHB-diglyceride and pure 3-BHB-triglyceride). Another part of the mixture is subjected to a separation by fractional distillation, so that on the one hand a first, low-boiling fraction is obtained, which comprises a high proportion of mono- and diglycerides of 3-hydroxybutyric acid and a low proportion of triglycerides of 3-hydroxybutyric acid, and on the other hand a second, high-boiling fraction, which comprises a low proportion of monoglycerides of 3-hydroxybutyric acid and a high proportion of di- and triglycerides of 3-hydroxybutyric acid.

The results of the fractionation are summarized in the following table (short path distillation, 0.01 mbar pressure, temperature of receiver vessel: 20° C., jacket temperature 83° C.):

|  | Raw mix % | Fraction I high-boiling % | Fraction II low-boiling % |
|---|---|---|---|
| 3-BHB-ethyl | 0.6 | 0.05 | 0.6 |
| 3-BHB-FS | 0.7 | 0.5 | 2.7 |
| glycerol | 1.3 | 0.4 | 10.2 |
| 3-BHB dimer | 3.4 | 0.7 | 27.2 |
| 3-BHB-MG | 18 | 15.8 | 45.8 |
| 3-BHB-dimer-MG | 0.5 | 0.3 | 2.6 |
| 3-BHB-DG | 53.3 | 57.8 | 10 |
| 3-BHB-TG | 15.2 | 16.7 | 0.6 |
| 3-BHB-dimer-DG | 6.3 | 6.8 | 0.2 |
| polymeric components | 0.9 | 1 | — |

Syntheses with Enzyme as Catalyst

In general, enzymes are well suited for the synthesis of 3-BHB glyceride mixtures according to the invention. They are highly selective and can be used under mild reaction conditions. Furthermore, enzymes are often enantioselective. Since 3-BHB—FS and its esters are bifunctional molecules (presence of an OH group and a carboxyl or ester group), conventional chemical esterification or transesterification conditions lead to increased and undesired by-product formation (e.g. oligo- or polymers, elimination reactions, etc.). In contrast, enzymes have the potential to bypass this potential by-product formation due to their high selectivity.

The following figure shows an example of the reaction scheme of an enzymatic esterification according to the invention (i.e. production of a 3-BHB-MG, 3-BHB-DG and 3-BHB-TG mixture by enzyme catalysis).

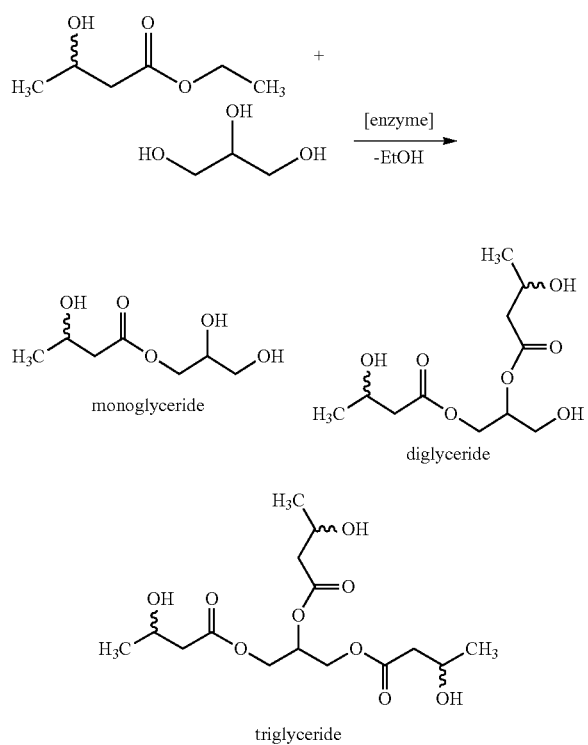

However, even when using enzymes, there may still be little by-product or secondary product formation. The following figure shows typical by-products formed during enzyme catalysis.

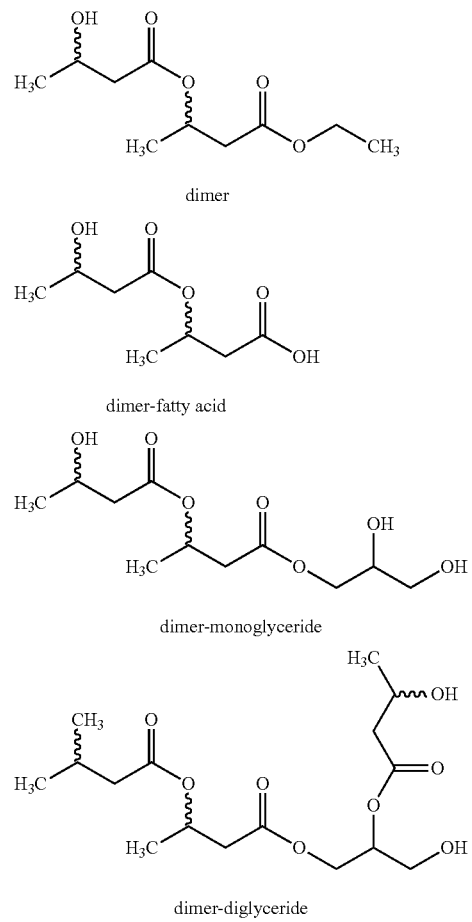

The by-products shown in the figure above are mainly secondary products. Without being bound to any theory, the formation of the respective dimer glycerides can possibly be explained by the fact that the respective dimer glycerides are formed from the dimer ethyl esters or that the 3-BHB monoglycerides and 3-BHB diglycerides are further transesterified at the OH group. The 3-BHB dimer acid (3-BHB-dimer-FS) occurs only in the presence of water and plays only a minor role, e.g. for a transesterification production process with 3-BHB ethyl, due to a possible vacuum process control.

Test Series with Enzymes

First, test series with enzymes are carried out to find suitable enzymes or suitable enzyme variants for the synthesis of 3-BHB glyceride mixtures according to the invention.

For this purpose, a test series for parallel examination of up to 4 approaches on a scale of 50 g to 100 g is first carried out. The experiments of the test series take place in Erlenmeyer flasks. These are kept in a water bath for 24 h at the desired temperature. The enzyme is then filtered out and recycled if necessary. The experiment is performed with and without a lid for each enzyme. The aim is to show the influence of the by-product ethanol on the chemical equilibrium.

The following table shows the results of an enzyme test series.

Results of an enzyme test series (50° C., 24 h, 1 wt.-% enzyme, 40 mol-% excess 3-BHB ethyl ester)

|  | 1<br>Novozym ® 435<br>closed system | 2<br>Novozym ® 435<br>open system | 3<br>Lipozym ® 435<br>closed system | 4<br>Lipozym ® 435<br>open system |
|---|---|---|---|---|
| 3-BHB-FS | 1.59 | 8.95 | 1.61 | 7.58 |
| 3-BHB dimer | 8.30 | 5.51 | 8.54 | 6.05 |
| 3-BHB-dimer-FS | n.d. | 2.15 | n.d. | 1.89 |
| 3-BHB-MG | 59.99 | 22.49 | 59.57 | 25.97 |
| 3-BHB-dimer-MG | n.d. | 0.84 | n.d. | 0.95 |
| 3-BHB-DG | 27.81 | 48.50 | 27.78 | 48.00 |
| 3-BHB-TG | 1.51 | 4.45 | 1.34 | 4.31 |
| 3-BHB-dimer-TG | 0.99 | 7.17 | 1.06 | 7.26 |
| polymers | n.d. | n.d. | n.d. | n.d. |

The table shows the composition of the reaction mixture after 24 h. The table shows the percentage composition without taking into account any educts that may still be comprised. The enzymes used are immobilized enzymes on polymeric carrier substances.

The results of the above enzyme test series show that Novozym® 435 and Lipozym® 435 provide high yields of 3-BHB-MG, 3-BHB-DG and 3-BHB-TG.

The experiments in the open system show an increased formation of 3-BHB—FS or 3-BHB-dimer-FS. This is due to the fact that—mainly caused by the evaporating water bath—unwanted water is present in the reaction mixture. However, this by-product formation is less important for a transesterification production method with 3-BHB ethyl, for example, since this can be carried out under vacuum.

Based on the findings of the hydrolysis side reaction, further test series experiments are carried out using CaCl$_2$) dry tubes. The results of these experiments are summarized in the following table.

Results when using dry tubes (70° C., 24 h, 1 wt-% enzyme)

|  | without enzyme | Lipozym ® 435 | Novozym ® 435 |
|---|---|---|---|
| 3-BHB-ethyl | 69.9 | 54.9 | 54.7 |
| 3-BHB-FS | 0.0 | 0.6 | 0.6 |
| glycerol | 26.4 | 8.2 | 8.2 |
| 3-BHB dimer | 0.7 | 2.7 | 2.8 |
| 3-BHB-dimer-FS | 0.0 | 0.0 | 0.0 |
| 3-BHB-MG | 3.2 | 21.5 | 21.6 |
| 3-BHB-dimer-MG | 0.0 | 0.0 | 0.0 |
| 3-BHB-DG | 0.1 | 11.0 | 11.1 |
| 3-BHB-TG | 0.0 | 0.7 | 0.7 |
| 3-BHB-dimer-DG | 0.0 | 0.3 | 0.4 |
| polymers | 0.0 | 0.1 | 0.1 |

The comparison of the two enzymes Novozym® 435 and Lipozym® 435 using a dry tube shows that hydrolysis takes place only to a very small extent. However, in terms of yield and selectivity, the results hardly differ from comparable experiments in a closed system. However, the pressure drop across the desiccant CaCl$_2$) is too high, so that hardly any ethanol can escape. However, the entry of water can be avoided. The results without enzyme show that the reaction can also be carried out autocatalytically. Small amounts of BHB-MG are also formed here.

Further investigations show that the enzymes are stereoselective. Especially, it can be deduced from a further analysis of the dimers that one enantiomer from the starting compound is preferentially converted, probably the (R)-enantiomer, so that a significantly increased proportion of (R)-3-hydroxybutyric acid or (R)-3-BHB is present in the products formed.

An NMR spectrum of the 3-BHB dimer (purified to >90% by column chromatography) confirms the enantioselectivity of the enzyme process. According to the NMR spectrum a diastereomer ratio of 56:44 is determined; according to GC analysis this ratio is 59:41.

Test Series with Starting Compound Surpluses

To test the activity of the two selected enzymes Novozym® 435 and Lipozym® 435 at different 3-BHB-ethyl ester surpluses, both enzymes are transesterified at 50° C. for 24 h equimolar and with 100 mol-% excess. The following table summarizes the results.

Results of the starting compound excess test series; 50° C., 24 h, 1 wt.-% enzyme

|  | 1<br>N. 435<br>equim.<br>g.S. | 2<br>N.435<br>equim<br>o.S. | 3<br>L 435<br>equim<br>g.S. | 4<br>L.435<br>equim<br>o.S. | 5<br>N. 435<br>100%<br>g.S. | 6<br>N.435<br>100%<br>o.S. | 7<br>L. 435<br>100%<br>g.S. | 8<br>L. 435<br>100%<br>o.S. |
|---|---|---|---|---|---|---|---|---|
| 3-BHB-FS | 1.25 | 9.01 | 1.28 | 9.42 | 2.23 | 13.83 | 2.09 | 11.66 |
| 3-BHB dimer | 4.95 | 2.04 | 5.24 | 2.16 | 13.23 | 10.51 | 13.60 | 11.64 |

TABLE-continued

Results of the starting compound excess test series;
50° C., 24 h, 1 wt.-% enzyme

| | 1<br>N. 435<br>equim.<br>g.S. | 2<br>N.435<br>equim<br>o.S. | 3<br>L 435<br>equim<br>g.S. | 4<br>L.435<br>equim<br>o.S. | 5<br>N. 435<br>100%<br>g.S. | 6<br>N.435<br>100%<br>o.S. | 7<br>L. 435<br>100%<br>g.S. | 8<br>L. 435<br>100%<br>o.S. |
|---|---|---|---|---|---|---|---|---|
| 3-BHB-dimer-FS | n.d. | 1.80 | n.d. | 2.12 | n.d. | 3.11 | n.d. | 3.22 |
| 3-BHB-MG | 67.59 | 32.63 | 67.26 | 32.34 | 50.91 | 20.03 | 50.94 | 17.69 |
| 3-BHB-dimer-MG | n.d. | 0.29 | n.d. | 0.38 | 0.71 | 1.34 | 0.72 | 1,80 |
| 3-BHB-DG | 24.64 | 45.49 | 24.60 | 44.26 | 29.75 | 41.66 | 29.61 | 42.25 |
| 3-BHB-TG | 0.89 | 3.07 | 0.88 | 3.05 | 1.78 | 3.61 | 1.69 | 4.32 |
| 3-BHB dimer-TG | 0.68 | 5.52 | 0.74 | 6.11 | 1.39 | 5.71 | 1.36 | 7.14 |
| polymer | n.d. | 0.16 | n.d. | 0.17 | n.d. | 0.19 | n.d. | 0.28 |

(closed system = g.S.; open system = o.S.; Novozym® 435 = N. 435; Lipozym® 435 = L 435)

The results show that the experiments in the open system, i.e. when distilling off ethanol, show a higher conversion to 3-BHB-DG or 3-BHB-TG. Furthermore, this series of experiments also shows increased hydrolysis in open reaction vessels (i.e. in an open system). Novozym® 435 and Lipozym® 435 show similar results under identical reaction conditions. Lipozym® 435 seems to be slightly more active than Novozym® 435.

Glycerol conversions are highest in the 100 mol-% surplus batches. However, the influence on the formation of 3-BHB dimers and the subsequent products (i.e. 3-BHB-dimer-MG and 3-BHB-dimer-DG) is clearly visible. With a 100 mol-% surplus, these products are formed two to four times as much, while the proportion of 3-BHB-TG is only about twice as high.

In summary, it can be stated that under the selected reaction conditions, an excess of 100 mol-% has a stronger influence on the by-product formation compared to the main product formation.

Test Series to Investigate Temperature and Substrate Effects

The influence of temperature as well as a first estimation of the influence of substrates on product formation are also investigated in test series experiments.

The reaction temperature is set to 70° C. In addition, 1 g of a high-boiling fraction from a KD distillation (see also above) is added to some preparations or experiments to investigate a first estimation of the influence of substrates on product formation.

The reaction mixture of these approaches mixed with the high-boiling fraction has the following initial composition:

| | initial composition with high-boiling fraction |
|---|---|
| 3-BHB-ethyl | 72.2 |
| 3-BHB-FS | <0.1 |
| glycerol | 24.3 |
| 3-BHB dimer | 0.7 |
| 3-BHB-dimer-FS | n.d. |
| 3-BHB-MG | 0.5 |
| 3-BHB-dimer-MG | n.d. |
| 3-BHB-DG | 1.6 |
| 3-BHB-TG | 0.2 |
| 3-BHB-dimer-DG | 0.4 |
| polymers | n.d. |

The following table shows the results of the substrate test series.

TABLE

Results of the substrate test series (70° C., 24 h, 1 wt.-% enzyme)

| | 1<br>N.<br>435<br>g.S. | 2<br>N.<br>435<br>o.S. | 3<br>L.<br>435<br>g.S. | 4<br>L.<br>435<br>o.S. | 5<br>N.<br>435<br>g.S. | 6<br>N.<br>435<br>o.S. | 7<br>L.<br>435<br>g.S. | 8<br>L.<br>435<br>o.S. |
|---|---|---|---|---|---|---|---|---|
| 3-BHB-FS | 1.65 | — | 1.71 | — | 1.70 | — | 1.71 | — |
| 3-BHB dimer | 8.89 | 5.30 | 8.48 | 4.87 | 7.77 | 3.86 | 7.58 | 4.07 |

TABLE-continued

Results of the substrate test series (70° C., 24 h, 1 wt.-% enzyme)

| | 1<br>N.<br>435<br>g.S. | 2<br>N.<br>435<br>o.S. | 3<br>L.<br>435<br>g.S. | 4<br>L.<br>435<br>o.S. | 5<br>N.<br>435<br>g.S. | 6<br>N.<br>435<br>o.S. | 7<br>L.<br>435<br>g.S. | 8<br>L.<br>435<br>o.S. |
|---|---|---|---|---|---|---|---|---|
| 3-BHB-dimer-FS | n.d. | 3.31 | n.d. | 3.61 | n.d. | 3.78 | n.d. | 3.22 |
| 3-BHB-MG | 55.63 | 16.54 | 55.78 | 13.47 | 55.64 | 14.96 | 56.10 | 14.43 |
| 3-BHB-dimer-MG | 0.35 | 1.03 | 0.31 | 0.86 | 0.33 | 0.74 | 0.31 | 0.83 |
| 3-BHB-DG | 30.42 | 43.90 | 30.69 | 45.19 | 31.42 | 44.36 | 31.23 | 45.17 |
| 3-BHB-TG | 2.07 | 10.64 | 2.05 | 11.31 | 2.13 | 11.36 | 2.11 | 12.60 |
| 3-BHB-dimer-DG | 0.98 | 8.20 | 0.99 | 8.32 | 1.01 | 8.41 | 0.97 | 9.20 |
| polymers | n.d. | 0.91 | n.d. | 0.87 | n.d. | 0.97 | n.d. | 1.15 |
| sum of by-products | 11.88 | 18.76 | 11.48 | 18.53 | 10.81 | 17.75 | 10.57 | 18.47 |
| | 40 mol-% | | | | 40 mol-% + 1 g high-boiling fraction | | | |

(closed system = g.S.; open system = o.S.; Novozym® 435 = N. 435; Lipozym® 435 = L. 435)

First of all, the influence of humidity and the resulting hydrolysis during the experiments in the open system is to be determined. The advantages of distilling off the resulting ethanol to shift the equilibrium become apparent. Lipozym® 435 and Novozym® 435 give very similar results with slightly higher activity for Lipozym® 435.

An influence of the added amount of products (1 g of a high-boiling fraction from a short path distillation) is not recognizable. The quantity adds up almost completely to the formed product quantity. For example, 3-BHB-DG is formed with Novozym® 435 (open system) with 35% without the addition of products and with 36.7% with the addition of products. This increase corresponds exactly to the added amount of 3-BHB-DG of 1.6% within the scope of the measuring accuracy.

The sum parameter of the by-products contains all dimers or dimer glycerides (see also above diagram). Free fatty acids or their dimers are irrelevant from a synthetic point of view, since hydrolysis plays only a minor role in a production process.

However, the results also show that a distilled educt fraction (3-BHB ethyl ester fraction) originating from a production process can be returned to the process without having a significant influence on the reaction.

In further test series under variation of the temperature, the influence of the temperature on the product formation can be determined. Compared to a reaction temperature of 50° C., for example, about 4% to 5% more 3-BHB-TG is formed (with simultaneous increase in glycerol conversion of about 25%).

The influence of an open system compared to a closed system is also evident: In a closed system, the formation of 3-BHB-MG is preferred over 3-BHB-DG, whereas in an open system this is more or less reversed. The formation of 3-BHB-TG and the by-products, on the other hand, remains more or less unaffected.

Test Series with Enzyme Recycling

In further series of test, the recyclability of the enzymes Novozym® 435 and Lipozym® 435 is investigated. For this purpose, the respective enzyme is filtered off from the previous experiment and the filter residue together with product adhesions is used for a further experiment.

It is shown that both enzymes can be recycled after 24 h at 70° C. After the first recycling cycle, the activity is hardly reduced and almost identical compositions are obtained. However, it is noticeable that both enzymes show a lower glycerol conversion after recycling, but at the same time form fewer dimers.

The following table shows the results obtained.

TABLE

Results of enzyme recycling (70° C., 24 h, 1 wt.-% enzyme, 40 mol-% excess BHB ethyl ester, all tests with dry tube)

| | Novozym ® 435 fresh | Novozym ® 435 recycled | Lipozym ® 435 fresh | Lipozym ® 435 recycled |
|---|---|---|---|---|
| 3-BHB-ethyl | 54.7 | 56.4 | 54.9 | 56.8 |
| 3-BHB-FS | 0.6 | 1.0 | 0.6 | 0.7 |
| glycerol | 8.2 | 8.8 | 8.2 | 8.8 |
| 3-BHB dimer | 2.8 | 1.6 | 2.7 | 1.5 |
| 3-BHB-dimer-FS | 0.0 | 0.0 | 0.0 | 0.0 |
| 3-BHB-MG | 21.6 | 21.6 | 21.5 | 21.6 |
| 3-BHB-dimer-MG | 0.0 | 0.0 | 0.0 | 0.0 |
| 3-BHB-DG | 11.1 | 10.0 | 11.0 | 10.0 |
| 3-BHB-TG | 0.7 | 0.5 | 0.7 | 0.5 |
| 3-BHB-dimer-DG | 0.4 | 0.2 | 0.3 | 0.2 |
| polymers | 0.1 | 0.0 | 0.1 | 0.0 |

Test Series with Investigation of the Enzyme Concentration

The influence of the enzyme concentration is also investigated in further series of tests. For this purpose, preparations with 0.1 wt.-%, 1 wt.-%, 5 wt.-% and 10 wt.-% of enzyme are prepared. The following table summarizes the results. The experiments were each performed with Novozym® 435 (open system).

The results show that the optimal concentration is in the range of about 1 wt.-% enzyme at 70° C. This is where the highest glycerol conversion is achieved. At higher enzyme concentrations the glycerol conversion decreases again. Furthermore, enzyme quantities of ≥5% lead to an increased formation of dimer-DG and higher dimer compounds. In all experiments, the increased proportion of BHB-FS and BHB-dimer-FS is due to the open experimental method (i.e. in an open system) in the water bath.

TABLE

Results of enzyme concentration test series
(70° C., 24 h, Novozym ® 435,
40 mol-% excess 3-BHB ethyl ester)

|  | 0.1 wt.-% | 1.0 wt.-% | 5.0 wt.-% | 10.0 wt.-% |
|---|---|---|---|---|
| 3-BHB-FS | 5.12 | 13.50 | 11.86 | 11.11 |
| 3-BHB dimer | 1.90 | 2.53 | 2.81 | 3.39 |
| 3-BHB-dimer-FS | 0.30 | 3.41 | 6.24 | 6.39 |
| 3-BHB-MG | 42.73 | 18.05 | 18.18 | 18.35 |
| 3-BHB-dimer-MG | 0.00 | 0.37 | 0.68 | 1.47 |
| 3-BHB-DG | 46.14 | 46.30 | 34.06 | 32.56 |
| 3-BHB-TG | 2.40 | 8.54 | 9.78 | 9.51 |
| 3-BHB-dimer-DG | 1.42 | 6.79 | 11.89 | 12.48 |
| polymers | — | 0.51 | 1.60 | 1.63 |
| unknown | — | — | 2.89 | 3.12 |
| sum of by-products | 8.73 | 27.10 | 35.09 | 36.46 |

Syntheses with Basic Metal Catalyst

Another possibility for the synthesis of 3-BHB glyceride mixtures is the chemical synthesis using metal catalysts, acids or bases. For this purpose, an esterification is carried out starting from the free fatty acid with elimination of water or, if the 3-BHB ethyl ester is used, a transesterification is carried out with separating off ethanol (in the presence of the catalyst). Within the scope of the present invention, the side reactions usually occurring in the prior art, especially oligo- and polymerization reactions, can be efficiently minimized or avoided by suitable reaction control.

The following reaction scheme shows a possible chemical synthesis of 3-BHB-glyceride mixtures by transesterification with basic catalyst according to the present invention.

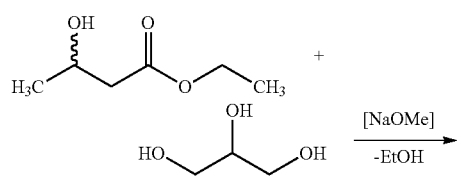

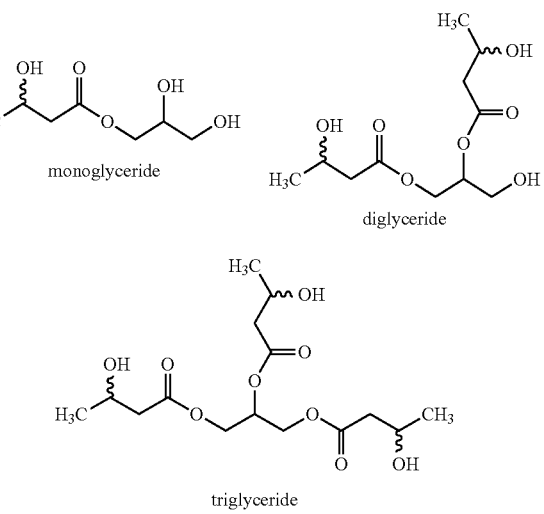

monoglyceride diglyceride triglyceride

The following table shows the results of a reaction of 3-BHB ethyl ester with sodium methylate (NaOMe) and glycerol.

TABLE

Results of the reaction of 3-BHB ethyl ester with sodium
methylate (NaOMe) and glycerol (100° C., 12 h,
1 wt.-% NaOMe, 40 mol-% excess BHB ethyl ester, vacuum)

| 3-BHB-methyl | 2.7 |
|---|---|
| 3-BHB-ethyl (educt) | 49.8 |
| 3-BHB-FS | 1.9 |
| glycerol | 13.4 |
| 3-BHB dimer | 4.2 |
| 3-BHB-dimer-FS | 0.0 |
| 3-BHB-MG | 20.6 |
| 3-BHB-dimer-MG | 0.2 |
| 3-BHB-DG | 6.8 |
| 3-BHB-TG | 0.3 |
| 3-BHB-dimer-DG | 0.2 |
| polymers | 0.0 |

It turns out that polymerization does not take place. Mono-, di- and triglycerides and small amounts of dimers are formed. A further addition of NaOMe and/or the implementation of a lower vacuum cannot increase the reaction progress any further, as a state of equilibrium or kinetic limitation seem to be reached, but selectively increasing only the amount of 3-BHB methyl ester, so that it can be assumed that the catalyst is still active and the reaction can be controlled in this way.

Physiological Application Tests: In-Vitro Digestion Tests

Digestion Experiments (Splitting or Cleavage Experiments) of Inventive

3-BHB Glyceride Mixtures

By means of cleavage experiments it is shown that 3-BHB esters or their mixtures, including reaction by-products such as dimers etc., produced according to the invention, can be cleaved in the human gastrointestinal tract. The starting mixture used is a crude high-boiling fraction from fractional distillation which has not been further purified and is obtained by the inventive method. This fraction contains a ternary mixture of 3-BHB-MG, 3-BHB-DG and 3-BHB-TG obtained according to the invention.

For the cleavage experiments under near-body conditions two media are investigated:

FaSSGF, which simulates the stomach
FaSSIF, which simulates the intestinal tract Both media are from the company Biorelevant®, Ltd. in Great Britain. In addition, in some experiments porcine pancreas is added (Panzytrat® 40,000, Fa. Allergan).

The results of the experiments are summarized in the following table (chromatographically determined, percentages determined as % area in the chromatogram).

TABLE

Results of the cleavage experiments in a FaSSGF or FaSSIF medium with Panzytrat ® (m.P.) and without Panzytrat ® (o.P.) (35° C., 24 h)

| | | FaSSGF (stomach, pH = 1.6) | | FaSSIF (bowel, pH = 6.5) | | |
|---|---|---|---|---|---|---|
| | before splitting % area | o.P. 24 h, 35° C. % area | m.P. 24 h, 35° C. % area | 0 h, Start % area | o.P. 24 h, 35° C. % area | m.P. 24 h, 35° C. % area |
| 3-BHB-ethyl | 0.31 | 0.07 | 0.11 | 0.16 | 0.18 | 0.20 |
| 3-BHB-FS | 0.43 | 26.21 | 18.85 | 0.04 | 0.02 | 2.60 |
| glycerol | 0.38 | 0.81 | 0.51 | 0.07 | 0.05 | 0.07 |
| 3-BHB dimer | 0.71 | 0.35 | 0.45 | 0.70 | 0.72 | 0.72 |
| 3-BHB-dimer-FS | n.d. | 3.25 | 2.51 | n.d. | n.d. | 0.17 |
| 3-BHB-MG | 18.28 | 21.09 | 18.41 | 13.52 | 12.26 | 14.34 |
| 3-BHB-dimer-MG | 0.39 | 0.16 | 0.22 | 0.42 | 0.44 | n.d. |
| 3-BHB-DG | 55.85 | 37.01 | 44.09 | 60.17 | 60.93 | 61.38 |
| 3-BHB-TG | 16.08 | 7.55 | 10.12 | 16.40 | 16.79 | 12.83 |
| 3-BHB-dimer-DG | 6.62 | 3.14 | 4.22 | 7.56 | 7.61 | 7.02 |
| polymers | 0.95 | 0.36 | 0.52 | 0.97 | 1.01 | 0.69 |

It is shown that the sample hydrolyses under FaSSGF conditions. This is mainly due to the low pH value (pH=1.6).

Under FaSSIF conditions, a small conversion or cleavage (2.6% 3-BHB—FS) takes place using Panzytrat®.

All experiments show that the cascade (3-BHB-TG becomes 3-BHB-DG, 3-BHB-DG becomes 3-BHB-MG, 3-BHB-MG becomes free acid and glycerol) continues. Furthermore, dimer acids (3-BHB-dimer-FS) are also formed. From this it can be seen that the dimer glycerides are also degraded. This can therefore be used for a possible pharmaceutical or pharmacological retardation effect.

Further Digestion Experiments (Cleavage Experiments) of Inventive
3-BHB Glyceride Mixtures
1. Cleavage Experiments with Pancreatin 2 g of a glyceride mixture prepared as described above based on mono-, di- and triglycerides of 3-hydroxybutyric acid are dissolved in 50 g water and 0.5 g (1 wt.-%) pancreatin is added.

The pancreatin is used in the form of the commercially available product Panzytrat® 40,000 from the Allergan company.

The whole mixture is stirred on a heating plate at 50° C.; the course of the reaction is determined and monitored by continuous recording of the acid number over time.

The acid number increases over a period of 1,250 min from the original 0.200 mg KOH/g to over 2.200 mg KOH/g (cleavage of the 3-BHB glycerides to form the free acid).

The conversion/time course of the aqueous cleavage of the glyceride mixture according to the invention by means of pancreatin, including an increase in the acid number over time, proves the desired decomposition of the educt mixture (glyceride mixture) to free acid. This is subsequently confirmed by appropriate analysis.

The experiment proves that the glyceride mixture of mono-, di- and triglycerides of 3-hydroxybutyric acid according to the invention is a suitable physiological precursor for 3-hydroxybutyric acid for the corresponding keto-body therapies.

The test is repeated and verified on the basis of the individual glycerides. Comparable results are obtained, i.e. both the monoglyceride and the diglyceride as well as the triglyceride of 3-hydroxybutyric acid are cleaved by pancreatin to the free 3-hydroxybutyric acid.

2. Cleavage with Gastric Medium: FaSSGF Medium

A so-called FaSSGF medium is prepared according to the manufacturer's specifications from the commercially available corresponding composition (available from Biorelevant, Ltd., Great Britain).

The resulting sample is divided into two batches of equal size. 10 wt.-% of the ternary glyceride mixture based on mono-, di- and triglycerides of 3-hydroxybutyric acid, as described hereinabove, is dissolved in each FaSSGF medium and left in a water bath at 35° C. for 24 hours. Additionally, to one of the two batches 1 wt.-% pancreatin (Panzytrat® 40,000) has previously been added.

For the purpose of analysis, the sample solutions are added to a CHROMABOND®-Xtr column for adsorption and allowed to act for >5 min and then eluted with 6 ml DCM (dichloromethane)/isopropanol (4:1).

The results of the cleavage experiment both with and without pancreatin in the FaSSGF medium show a strong increase in free 3-hydroxybutyric acid and a significant decrease in the di- and triglycerides of 3-hydroxybutyric acid in the FaSSGF medium both with and without pancreatin. Further analysis shows that the sample was split or decomposed as desired by the medium (pH value of the medium: 1.6).

The following table shows the results of the cleavage experiment with and without Panzytrat® 40,000 in FaSSGF medium.

TABLE

Results of the cleavage experiments with and without Panzytrat ® 40,000 in a FaSSGF medium

| | % area | % area | % area |
|---|---|---|---|
| 3-BHB-ethyl | 0.31 | 0.07 | 0.11 |
| 3-BHB-FS | 0.43 | 26.21 | 18.85 |
| glycerol | 0.38 | 0.81 | 0.51 |
| 3-BHB dimer | 0.71 | 0.35 | 0.45 |
| 3-BHB-dimer-FS | n.d. | 3.25 | 2.51 |
| 3-BHB-MG | 18.28 | 21.09 | 18.41 |
| 3-BHB-dimer-MG | 0.39 | 0.16 | 0.22 |
| 3-BHB-DG | 55.85 | 37.01 | 44.09 |
| 3-BHB-TG | 16.08 | 7.55 | 10.12 |
| 3-BHB-dimer-DG | 6.62 | 3.14 | 4.22 |
| polymers | 0.95 | 0.36 | 0.52 |
| | before splitting | without Panzytrat ® | with Panzytrat ® |

3. Cleavage with Bowl Medium: FaSSIF Medium

The FaSSIF medium is prepared according to the manufacturer's instructions (Fa. Biorelevant, Ltd., Great Britain).

The sample obtained is divided into two equally sized preparations. 10 wt.-% of the aforementioned glyceride mixture based on a mixture of mono-, di- and triglycerides of 3-hydroxybutyric acids is dissolved in each FaSSIF medium and left in a water bath at 35° C. for 24 hours. An additional 1 wt.-% of pancreatin (Panzytrat® 40,000) has been added to one of the two preparations beforehand.

For the purpose of analysis, 0.5 ml of sample solution each is added to a CHROMABOND® Xtr column for adsorption and allowed to act for 5 min and then eluted with 6 ml DCM/isopropanol (4:1).

The results of the cleavage experiment with and without pancreatin in the FaSSIF medium show a slight increase in free 3-hydroxybutyric acid and a corresponding slight decrease in the content of triglycerides of the 3-hydroxybutyric acid of the starting mixture, which proves an enzymatic degradation or decomposition of the sample, which is confirmed by further analysis.

The pH value of the FaSSIF medium is 6.5. The FaSSIF medium itself does not seem to favor cleavage.

The following table shows the results of the cleavage experiment in the FaSSIF medium.

TABLE

Results of the cleavage experiment with and without Panzytrat ® 40,000 in a FaS-SIF medium.

|  | before splitting 0 h | without Panzytrat ® 24 h, 35° C. | with Panzytrat ® 24 h, 35° C. |
|---|---|---|---|
| 3-BHB-ethyl | 0.16 | 0.18 | 0.20 |
| 3-BHB-FS | 0.04 | 0.02 | 2.60 |
| glycerol | 0.07 | 0.05 | 0.07 |
| 3-BHB dimer | 0.70 | 0.72 | 0.72 |
| 3-BHB-dimer-FS | 0.00 | 0.00 | 0.17 |
| 3-BHB-MG | 13.52 | 12.26 | 14.34 |
| 3-BHB-dimer-MG | 0.42 | 0.44 | 0.00 |
| 3-BHB-DG | 60.17 | 60.93 | 61.38 |
| 3-BHB-TG | 16.40 | 16.79 | 12.83 |
| 3-BHB-dimer-DG | 7.56 | 7.61 | 7.02 |
| polymers | 0.97 | 1.01 | 0.69 |

4. Further Cleavage with Bowl Medium: FaSSIF Medium

The FaSSIF medium is prepared according to the previous test according to the manufacturer's instructions.

The resulting sample is divided into two batches of equal size. 10 wt.-% of the ternary glyceride mixture of mono-, di- and triglycerides of 3-hydroxybutyric acids according to the invention is dissolved in each FaSSIF medium and left in a water bath at 35° C. for 24 hours. To one batch, 1 wt.-% of a porcine pancreatic lipase type II (PPL type II) has been added beforehand.

For the purposes of analysis, 0.5 ml sample solution is added to a CHROMABOND® Xtr column for adsorption and allowed to act for more than 5 min, then eluted with 6 ml DCM/isopropanol (4:1).

The results of the cleavage experiment with porcine pancreatic lipase in FaSSIF medium show a slight increase in free 3-hydroxybutyric acid and a corresponding slight decrease in the content of triglyceride of 3-hydroxybutyric acid, which indicates enzymatic degradation or decomposition of the sample, which is confirmed by further analysis.

The pH value of the FaSSIF medium is 6.5, and the FaSSIF medium itself does not seem to favor cleavage.

The following table shows the results of the cleavage experiment with and without pancreatic lipase type II in FaSSIF medium.

TABLE

Results of cleavage experiments with and without porcine pancreatic lipase in a FaSSIF medium

|  | before splitting 0 h | without enzyme 24 h, 35° C. | with enzyme, 24 h, 35° C. |
|---|---|---|---|
| 3-BHB-ethyl | 0.16 | 0.18 | 0.12 |
| 3-BHB-FS | 0.04 | 0.02 | 1.79 |
| glycerol | 0.07 | 0.05 | 0.08 |
| 3-BHB dimer | 0.70 | 0.72 | 0.71 |
| 3-BHB-dimer-FS | 0.00 | 0.00 | 0.17 |
| 3-BHB-MG | 13.52 | 12.26 | 15.98 |
| 3-BHB-dimer-MG | 0.42 | 0.44 | 0.16 |
| 3-BHB-DG | 60.17 | 60.93 | 59.84 |
| 3-BHB-TG | 16.40 | 16.79 | 13.38 |
| 3-BHB-dimer-DG | 7.56 | 7.61 | 7.07 |
| polymers | 0.97 | 1.01 | 0.70 |

The previously described cleavage experiments prove that mono-, di- and/or triglycerides of 3-hydroxybutyric acid are efficient precursors or metabolites of free hydroxybutyric acid or its salts, especially with regard to their intended effect, which are present in physiologically compatible or physiologically compatible form.

The invention claimed is:

1. A method for producing a mixture of mono-, di- and triglycerides of 3-hydroxybutyruic acid of the general formula (III):

$$CH_2(OR^2)\text{---}CH(OR^3)\text{---}CH(OR^4) \qquad (III),$$

comprising reacting at least one compound of the general formula (I):

$$CH_3\text{---}CH(OH)\text{---}CH_2\text{---}C(O)OR^1 \qquad (I),$$

with glycerol, wherein:
   the reaction is carried out in the presence of an enzyme as catalyst;
   the reaction is carried out in the absence of any solvent;
   $R^1$ is selected from the group consisting of H or $C_1$-$C_4$ alkyl;
   $R^2$, $R^3$ and $R^4$, each independently of one another, is selected from H or a radical of formula $CH_3$---CH(OH)---$CH_2$---C(O)---, provided that at least one of $R^2$, $R^3$ and $R^4$, is not H; and
   the mixture comprises monoglycerides of 3-hydroxybutyric acid (3-BHB-MG), diglycerides of 3-hydroxybutyric acid (3-BHB-DG) and triglycerides of 3-hydroxybutyric acid (3-BHB-TG), in a weight ratio of 3-BHB-MG/3-BHB-DG/3-BHB-TG in the range of 10-80/10-70/0.1-20.

2. The method according claim 1, wherein the compound of general formula (I), is $CH_3$---CH(OH)---$CH_2$---C(O)$OC_2H_5$.

3. The method according to claim 1,
   wherein the catalyst is recycled after the reaction.

4. The method according to claim 1,
   wherein the enzyme is selected from the group consisting of synthetases, catalases, esterases, lipases and combinations thereof.

5. The method according to claim 1,
   wherein the enzyme is derived from the group consisting of *Candida antarctica, Mucor miehei, Thermomyces lanuginosus, Candida rugosa, Aspergillus oryzae, Pseudomonas cepacia, Pseudomonas fluorescens, Rhizopus delemar* and *Pseudomonas* sp. and combinations thereof; and wherein the enzyme is used in immobilized form on a carrier.

6. The method according to claim 1, wherein the reaction is carried out at temperatures in the range of from 10° C. to 80° C.

7. The method according claim 1, wherein the amount of the enzyme used is from 0.001 to 20% by weight.

8. The method according to claim 1, wherein the molar ratio of the compound of formula (I) to glycerol is from 1:1 to >200:1.

9. The method according to claim 8, wherein the molar ratio of the compound of formula (I) to glycerol is from 1:1 to 10:1.

10. The method according claim 1, wherein the weight ratio of 3-BHB-MG/3-BHB-DG/3-BHB-TG is in the range of 20-70/20-60/0.5-15.

11. A mixture of mono-, di- and triglycerides of 3-hydroxybutyruic acid of the general formula (III):

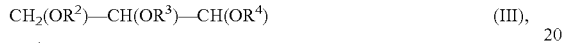

$$CH_2(OR^2)\text{—}CH(OR^3)\text{—}CH(OR^4) \quad (III),$$

wherein:
R$^2$, R$^3$ and R$^4$, each independently of one another, is selected from H or a radical of formula CH$_3$—CH(OH)—CH$_2$—C(O)—, provided that at least one of R$^2$, R$^3$ and R$^4$, is not H; and the mixture comprises monoglycerides of 3-hydroxybutyric acid (3-BHB-MG), diglycerides of 3-hydroxybutyric acid (3-BHB-DG) and triglycerides of 3-hydroxybutyric acid (3-BHB-TG), in a weight ratio of 3-BHB-MG/3-BHB-DG/3-BHB-TG in the range of 10-80/10-70/0.1-20.

12. The mixture according claim 11, wherein the weight ratio of 3-BHB-MG/3-BHB-DG/3-BHB-TG is in the range of 20-70/20-60/0.5-15.

13. A pharmaceutical composition comprising a mixture of mono-, di- and triglycerides of 3-hydroxybutyruic acid of the general formula (III):

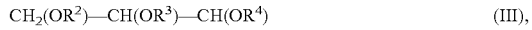

$$CH_2(OR^2)\text{—}CH(OR^3)\text{—}CH(OR^4) \quad (III),$$

wherein:
R$^2$, R$^3$ and R$^4$, each independently of one another, is selected from H or a radical of formula CH$_3$—CH(OH)—CH$_2$—C(O)—, provided that at least one of R$^2$, R$^3$ and R$^4$, is not H; and the mixture comprises monoglycerides of 3-hydroxybutyric acid (3-BHB-MG), diglycerides of 3-hydroxybutyric acid (3-BHB-DG) and triglycerides of 3-hydroxybutyric acid (3-BHB-TG), in a weight ratio of 3-BHB-MG/3-BHB-DG/3-BHB-TG in the range of 10-80/10-70/0.1-20.

14. The pharmaceutical composition according to claim 13, wherein the pharmaceutical composition is a drug or a medicament.

15. A food product comprising a mixture of mono-, di- and triglycerides of 3-hydroxybutyruic acid of the general formula (III):

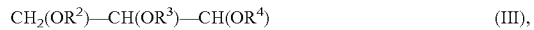

$$CH_2(OR^2)\text{—}CH(OR^3)\text{—}CH(OR^4) \quad (III),$$

wherein:
R$^2$, R$^3$ and R$^4$, each independently of one another, is selected from H or a radical of formula CH$_3$—CH(OH)—CH$_2$—C(O)—, provided that at least one of R$^2$, R$^3$ and R$^4$, is not H; and the mixture comprises monoglycerides of 3-hydroxybutyric acid (3-BHB-MG), diglycerides of 3-hydroxybutyric acid (3-BHB-DG) and triglycerides of 3-hydroxybutyric acid (3-BHB-TG), in a weight ratio of 3-BHB-MG/3-BHB-DG/3-BHB-TG in the range of 10-80/10-70/0.1-20.

16. The food product according to claim 15, wherein the food product is prepared for the application for catabolic metabolic states selected from the group consisting of hunger, diets and low-carbohydrate nutrition.

* * * * *